United States Patent
Wang et al.

(10) Patent No.: US 11,584,700 B2
(45) Date of Patent: Feb. 21, 2023

(54) METHODS FOR OPERATING ACETYLENE HYDROGENATION UNITS IN OLEFIN PRODUCTION PROCESSES

(71) Applicant: Dow Global Technologies LLC, Midland, MI (US)

(72) Inventors: Hangyao Wang, Freeport, TX (US); Yu Liu, Freeport, TX (US); Ernest R. Frank, Freeport, TX (US); Lin Luo, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/433,800

(22) PCT Filed: Feb. 4, 2020

(86) PCT No.: PCT/US2020/016464
§ 371 (c)(1),
(2) Date: Aug. 25, 2021

(87) PCT Pub. No.: WO2020/176200
PCT Pub. Date: Sep. 3, 2020

(65) Prior Publication Data
US 2022/0135498 A1    May 5, 2022

Related U.S. Application Data

(60) Provisional application No. 62/811,660, filed on Feb. 28, 2019.

(51) Int. Cl.
*C07C 5/09*    (2006.01)
(52) U.S. Cl.
CPC .................... *C07C 5/09* (2013.01)

(58) Field of Classification Search
CPC ...................................................... C07C 5/09
See application file for complete search history.

(56) References Cited

U.S. PATENT DOCUMENTS 3,128,317 A * 4/1964 Arkell ................... C07C 5/08
585/262
3,839,483 A * 10/1974 Carr et al. ............ C07C 5/09
208/143

(Continued)

FOREIGN PATENT DOCUMENTS

JP    4395369 B2    1/2010

OTHER PUBLICATIONS

International Search Report and Written Opinion issued by the European Patent Office acting as International Searching Authority for International Patent Application No. PCT/US2020/016464 dated Jun. 18, 2020 (12 total pages).

(Continued)

*Primary Examiner* — Thuan D Dang
(74) *Attorney, Agent, or Firm* — Dinsmore & Shohl LLP

(57) ABSTRACT

A method for selectively hydrogenating acetylene in a cracked gas from a steam cracking unit for producing olefins may include separating a hydrogenation feed from the cracked gas. The hydrogenation feed may include acetylene, hydrogen, carbon monoxide, and at least one product. The method may further include contacting the hydrogenation feed with an acetylene hydrogenation catalyst, the contacting causing hydrogenation of at least a portion of the acetylene of the hydrogenation feed to produce a hydrogenation effluent. In response to a change in a composition of a feedstock to the steam cracking unit that results in a change in a hydrogen concentration in the hydrogenation feed, the method may further include determining the hydrogen concentration in the hydrogenation feed and increasing or (Continued)

decreasing a temperature of the hydrogenation feed based on the determined hydrogen concentration of the hydrogenation feed.

17 Claims, 5 Drawing Sheets

(56) References Cited

U.S. PATENT DOCUMENTS

| | | | |
|---|---|---|---|
| 4,241,230 A | * | 12/1980 | Drinkard .............. B01J 19/0033 422/62 |
| 8,747,656 B2 | | 6/2014 | Tonkovich et al. |
| 9,926,496 B2 | | 3/2018 | Tonkovich et al. |
| 2010/0152507 A1 | | 6/2010 | Gajda |
| 2013/0102819 A1 | | 4/2013 | Szesni et al. |
| 2014/0163273 A1 | | 6/2014 | Keusenkothen |

OTHER PUBLICATIONS

Communication pursuant to Rules 161(1) and 162 EPC for Application No. 20713413.1 dated Oct. 8, 2021, pp. 1 to 3.
International Preliminary Report on Patentability for Application No. PCT/US2020/016464 dated Aug. 25, 2021, pp. 1 to 6.
Communication pursuant to Article 94(3) EPC, pertaining to European Patent Application No. 20713413.1, dated Oct. 7, 2022, 4 pages.

* cited by examiner

METHODS FOR OPERATING ACETYLENE HYDROGENATION UNITS IN OLEFIN PRODUCTION PROCESSES

CROSS-REFERENCE TO RELATED APPLICATIONS

This application is a National Stage Entry under 35 U.S.C. § 371 of International Patent Application No. PCT/US2020/016464, entitled "METHODS FOR OPERATING ACETYLENE HYDROGENATION UNITS IN OLEFIN PRODUCTION PROCESSES", filed Feb. 4, 2020, which claims priority to U.S. Provisional Patent Application No. 62/811,660, entitled "METHODS FOR OPERATING ACETYLENE HYDROGENATION UNITS IN OLEFIN PRODUCTION PROCESSES," filed on Feb. 28, 2019, the entire disclosures of both of which are hereby incorporated by reference in the present application.

BACKGROUND

Field

The present disclosure generally relates to chemical processing systems for producing olefins and the operation thereof and, more specifically, to methods for operating acetylene hydrogenation units in olefin production processes.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as a product stream from a petrochemical operation. For example, hydrocarbon cracking (e.g., steam cracking) may be used to produce olefins from a hydrocarbon stream. However, hydrocarbon cracking and other processes for producing light olefins can produce byproducts and impurities, such as acetylenic and allenic compounds, which can be poisons to downstream processes and catalysts. Additionally, the presence of high concentrations of acetylene may present a safety concern in downstream processes due to the reactivity of these compounds. Acetylene and other impurities and byproducts can be removed from an olefin containing hydrocarbon cracking effluent through hydrogenation in a selective hydrogenation process downstream of the hydrocarbon cracking unit. Selective hydrogenation of acetylene compounds in the hydrocarbon cracking effluent can also recover additional product olefins, such as ethylene and propylene.

SUMMARY

Current processes for selectively hydrogenating acetylene in an olefin production process are designed to operate with a relative stable feed stream having little variation in hydrogen concentration introduced to the hydrogenation unit. Such systems may operate smoothly with a steam cracker effluent that has little variation in composition due to the constant composition of the hydrocarbon feedstock. The composition of the steam cracker effluent and the composition of the feed stream to the acetylene hydrogenation unit are generally predictable, based at least on the composition of the hydrocarbon feedstock introduced to the steam cracking unit. However, fluctuation in the hydrocarbons market may lead to frequent change of feedstocks introduced to the steam cracking unit. Changing feedstock compositions and operating conditions of the steam cracking units may cause the hydrogen concentration of the feed to the acetylene hydrogenation unit to vary relative to the operation of the acetylene hydrogenation unit under constant feedstock composition. For example, switching the feedstock to the steam cracking unit to a lighter hydrocarbon stream for steam cracking, such as a stream comprising a greater concentration of ethane relative to propane and/or naphtha, can produce a cracking effluent having a greater concentration of hydrogen compared to the heavier hydrocarbon streams with lesser concentrations of ethane and greater concentrations of propane and naphtha. Increasing the concentration of hydrogen in the cracking effluent may lead to lower olefin selectivity in acetylene hydrogenation operation at constant inlet temperature, resulting in hydrogenation of a portion of the olefin products, such as ethylene and propylene, produced in the steam cracking unit, to corresponding paraffinic compounds. Rapid increases in hydrogenation of olefins, such as ethylene and propylene, may cause thermal runaway of the acetylene hydrogenation unit due to rapid heat release from the olefin hydrogenation reactions, which are exothermic. Decreasing the concentration of hydrogen in the cracker effluent to maintain a constant hydrogen concentration is possible, for example by applying a pressure swing adsorption unit. However, the capital and operating costs for such an operation can be excessively high and, therefore, in practice, this approach is possible but rare.

Additionally, when the feedstock to the steam cracker changes again from a lighter feedstock to a heavier feedstock having a greater concentration of naphtha and propane and less ethane, the hydrogen concentration may decrease. In this situation, the sudden reduction in the hydrogen concentration in the input to the hydrogenation unit due to a change in feedstock to the steam cracker may cause a shift in the process window of the acetylene hydrogenation unit toward lower conversion of acetylene, which can lead to breakthrough of acetylene to downstream processes. Breakthrough of acetylene to downstream processes can result in ethylene product streams that fail to meet specifications. The presence of acetylene in product streams may cause additional problems in downstream processes utilizing these ethylene product streams.

The methods disclosed herein for operating an acetylene hydrogenation unit in an olefin production process may reduce or prevent acetylene breakthrough and/or thermal runaway by changing the operating conditions of the acetylene hydrogenation unit in response to changes in the hydrogen concentration in the acetylene hydrogenation unit or the streams fed thereto. In particular, in one or more embodiments presently described, the methods may include determining the hydrogen concentration in the acetylene hydrogenation unit or the hydrogenation feed and modifying the temperature, the carbon monoxide (CO) concentration, or both, in the acetylene hydrogenation unit to meet the desired acetylene target concentrations without risk of reactor runaway or breakthrough of acetylene to downstream processes. It has been discovered that modifying the temperature of the acetylene hydrogenation unit and/or the CO concentration in the acetylene hydrogenation unit shifts operation of the acetylene hydrogenation unit with respect to acetylene conversion and ethylene selectivity, which may be leveraged to reduce the probability of thermal runaway or breakthrough of the acetylene to downstream processes. The inlet temperature of the acetylene hydrogenation unit may be increased or decreased by increasing or decreasing the temperature of the hydrogenation feed introduced to the acetylene hydrogenation unit, such as by changing the amount of heat transferred to the hydrogenation feed before passing it into the acetylene hydrogenation unit. The CO concentration in the acetylene hydrogenation unit may be increased or decreased by changing the operating conditions of the steam cracking unit or the concentration of sulfur-containing compounds in the steam cracking unit upstream of the acetylene hydrogenation unit. Supplemental CO may also be added to the hydrogenation feed before passing the hydrogenation feed to the acetylene hydrogenation unit. Accordingly, there is an ongoing need for processes for operating acetylene hydrogenation units in olefin production processes that enable frequent changes in the composition of the feedstock introduced to the olefin production process while preventing thermal runaway of the acetylene hydrogenation unit.

According to one embodiment presently described, a method for selectively hydrogenating acetylene in a cracked gas from a steam cracking unit for producing olefins may include separating a hydrogenation feed from the cracked gas. The hydrogenation feed may include acetylene, hydrogen, carbon monoxide, and at least one product (e.g., at least one olefin product). The method may further include contacting the hydrogenation feed with an acetylene hydrogenation catalyst, the contacting causing hydrogenation of at least a portion of the acetylene of the hydrogenation feed to produce a hydrogenation effluent. In response to a change in a composition of a feedstock to the steam cracking unit that results in a change in a hydrogen concentration in the hydrogenation feed, the method may further include determining the hydrogen concentration in the hydrogenation feed and increasing or decreasing a temperature of the hydrogenation feed based on the determined hydrogen concentration of the hydrogenation feed.

According to another embodiment presently described, a method for operating an acetylene hydrogenation unit in an olefin production system may include cracking at least a portion of a feedstock in a steam cracking unit to produce a cracked gas. The feedstock may include one or more hydrocarbons. The method may further include passing at least a portion of the cracked gas to a separation system operable to produce at least a hydrogenation feed from the cracked gas. The hydrogenation feed may include at least acetylene, carbon monoxide, hydrogen, and at least one product (e.g., at least one olefin product). The method may further include contacting the hydrogenation feed with an acetylene hydrogenation catalyst in an acetylene hydrogenation unit, the contacting causing hydrogenation of at least a portion of the acetylene in the hydrogenation feed to produce a hydrogenation effluent. The method may further include changing a composition of the feedstock cracked in the steam cracking unit. Changing the composition of the feedstock may increase or decrease a hydrogen concentration in the hydrogenation feed. The method may further include, in response to changing the composition of the feedstock, determining the hydrogen concentration in the acetylene hydrogenation unit and increasing or decreasing a temperature of the acetylene hydrogenation unit based on the determination of the hydrogen concentration in the acetylene hydrogenation unit.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
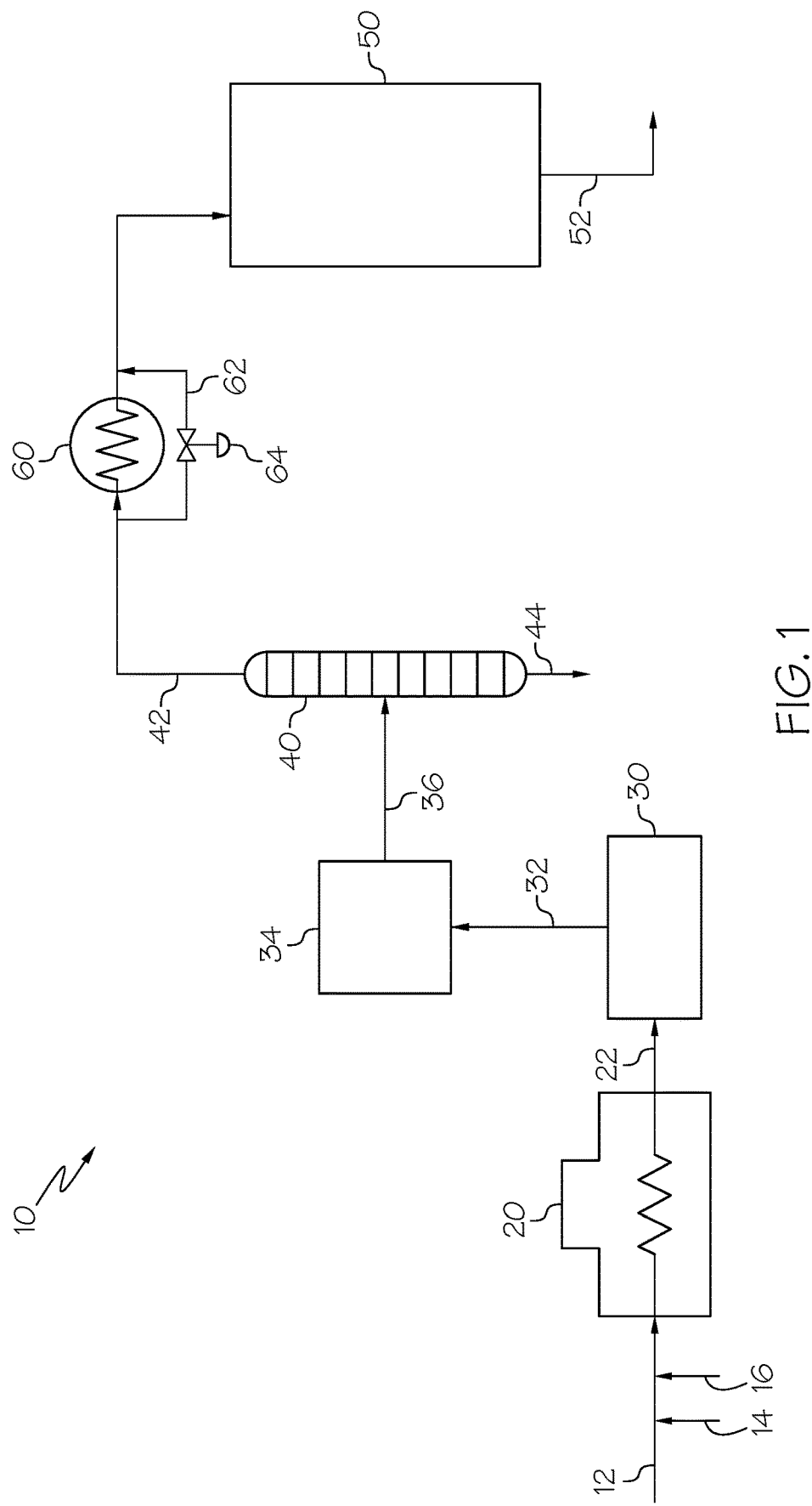
FIG. 1 schematically depicts a process for producing olefins from a hydrocarbon feedstock, the process including a heat exchanger upstream of an acetylene hydrogenation unit, according to one or more embodiments shown an described herein.

It should be understood that the drawings are schematic in nature, and may not include some components of reactor systems commonly employed in the art, such as, without limitation, sensors, temperature transmitters, pressure transmitters, flow meters, pumps, valves, heat exchangers, internal reactor structures, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

One or more embodiments of the present disclosure are directed to methods for operating an acetylene hydrogenation unit in an olefin production process. In particular, one or more embodiments of the present disclosure are directed to methods for operating the acetylene hydrogenation unit of the olefin production process when the composition of the feedstock to the olefin production process frequently changes. According to one or more embodiments, the methods disclosed herein for selectively hydrogenating acetylene in a cracked gas from a steam cracking unit for producing olefins may include separating a hydrogenation feed from the cracked gas, the hydrogenation feed comprising acetylene, hydrogen, carbon monoxide, and at least one product. The method may further include contacting the hydrogenation feed with an acetylene hydrogenation catalyst, the contacting causing hydrogenation of at least a portion of the acetylene of the hydrogenation feed to produce a hydrogenation effluent. In response to a change in a composition of a feedstock to the steam cracking unit that results in a change in a hydrogen concentration in the hydrogenation feed, the method may further include, determining a hydrogen concentration in the hydrogenation feed and increasing or decreasing a temperature of the hydrogenation feed based on the determined hydrogen concentration of the hydrogenation feed. The method may further include increasing or decreasing a concentration of CO in the hydrogenation feed in response to the determined hydrogen concentration in the hydrogenation feed or the hydrogenation effluent. The methods of the present disclosure may enable the operating parameters of the acetylene hydrogenation unit to be modified to accommodate frequent changes in the concentrations of hydrogen in the hydrogenation feed caused by changes in hydrocarbon feedstock to the steam cracking unit, while reducing or preventing thermal runaway and maintaining conversion of acetylene to reduce or prevent breakthrough of acetylene to downstream processes.

As used herein, the term "hydrogenation feed" refers to an effluent from the separation system passed to the acetylene hydrogenation unit that includes at least 95% by mass of the acetylene from the cracked gas introduced to the separation system.

As used herein, the term "acetylene-depleted stream" refers to another effluent stream from the separation system that includes less than 5% by mass of the acetylene from the cracked gas passed to the separation system.

As used herein, the terms "upstream" and "downstream" are relative to the direction of flow of materials through the process. For example, a first unit operation is upstream of a second unit operation if one or more material streams flow from the first unit operation to the second unit operation. The first unit operation is downstream of the second unit operation if one or more material streams flow from the second unit operation to the first unit operation.

As used herein, the term "selectivity" may refer to a ratio of a change in the moles of a desired product produced by a process to the moles of a reactant consumed by the process. For example, the ethylene selectivity of the acetylene hydrogenation unit may be a ratio of the change in the moles of ethylene produced in the acetylene hydrogenation unit divided by the total moles of acetylene consumed by the acetylene hydrogenation reaction. For example, if all acetylene is converted to ethylene, the selectivity is 100%. If all acetylene is converted to ethane, the selectivity is 0 (zero). And if not only all acetylene but also some of incoming ethylene is converted to ethane, the selectivity then becomes negative. Thus, the selectivity for ethylene can be expressed by the following Equation 1 (EQU. 1):

$$S_{C_2H_4} = \frac{(n_{C_2H_4 out} - n_{C_2H_4 in})}{(n_{C_2H_2 in} - n_{C_2H_2 out})} \quad \text{EQU. 1}$$

In EQU. 1, $S_{C_2H_4}$ is the selectivity for ethylene; $n_{C_2H_4out}$ is the moles of ethylene in the effluent passed out of the acetylene hydrogenation unit; $n_{C_2H_4in}$ is the moles of ethylene in the feed to the acetylene hydrogenation unit; $N_{C_2H_2in}$ is the moles of acetylene in the feed to the acetylene hydrogenation unit; and $n_{C_2H_2out}$ is the moles of acetylene in the effluent passed out of the acetylene hydrogenation unit.

As used herein, the term "breakthrough" may refer to passing of a specific reactant, such as but not limited to, acetylene, methyl acetylene, propadiene, or other compound, from one processing unit to another downstream processing unit in an amount greater than a threshold value specified by the olefin users, for example 2 parts per million by volume (ppmv). In an example, breakthrough may occur when the specific reactant undergoes substantially incomplete conversion in a reaction system so that an effluent passed out of the reaction system has a concentration of the specific reactant of greater than 2 part per million by volume (ppmv), or greater than 1 ppmv depending on olefin users and the location.

As used herein, the term "thermal runaway" may refer to a condition of a process in which the process is accelerated by an incremental increase in the temperature of the process, which changes the operating conditions of the process in a manner that produces or generates additional heat or energy, which further increases the temperature.

Referring to FIG. 1, a process 10 for producing olefins through hydrocarbon steam cracking is schematically depicted. The process 10 may include a hydrocarbon cracking unit 20, a quench process 30 downstream of the hydrocarbon cracking unit 20, an acid gas removal unit 34, a separation system 40 downstream of the quench unit 30 and acid gas removal unit 34, and an acetylene hydrogenation unit 50 downstream of the separation system 40. The acetylene hydrogenation unit 50 may be positioned to receive a hydrogenation feed 42 from the separation system 40. A hydrocarbon feedstock 12 may be introduced to the hydrocarbon cracking unit 20 for cracking one or more constituents of the hydrocarbon feedstock 12 to produce one or more olefins. The hydrocarbon feedstock 12 may be any hydrocarbon stream, such as a product stream from a petrochemical process or a refining operation for crude oil, shale gas, or other hydrocarbon sources. In some embodiments, the hydrocarbon feedstock 12 may include a plurality of different hydrocarbon streams combined prior to or in the hydrocarbon cracking unit 20. In some embodiments, the hydrocarbon feedstock 12 may be a light hydrocarbon feedstock, such as a feedstock including ethane, propane, butane, naphtha, other light hydrocarbon, or combinations of these.

The hydrocarbon cracking unit 20 may be operable to receive the hydrocarbon feedstock 12 and crack one or more constituents of the hydrocarbon feedstock 12 to produce a cracker effluent 22. The hydrocarbon cracking unit 20 may be a steam cracking unit, in which the hydrocarbon feedstock 12 is contacted with steam at temperatures of from 500° C. to 850° C. to produce the cracker effluent 22. In some embodiments, the hydrocarbon cracking unit 20 may be a steam cracking unit, and the hydrocarbon feedstock 12 may be a light hydrocarbon composition that may include ethane, propane, naphtha, or combinations of these as well as other hydrocarbons. A sulfur-containing composition 14, oxygenate-containing stream 16, or both may also be introduced to the hydrocarbon cracking unit 20. The sulfur-containing composition 14 may include one or more sulfur-containing compounds, such as, but not limited to dimethyl disulfide (DMDS), dimethyl sulfide (DMS), diethyl disulfide (DES), methyl mercaptan (MM), or combinations thereof. The sulfur-containing compounds may passivate the heating coil in the steam cracking furnace of the steam cracking unit to manage the formation of coke in the steam cracking unit. Increasing or decreasing the sulfur-containing compounds may change the amount of CO generated in the steam cracker, thereby changing the CO concentration in the cracker effluent 22. The oxygenate-containing stream 16 may include one or a plurality of oxygenates, such as but not limited to alcohols. In embodiments, the oxygenate-containing stream 16 may be a methanol-containing stream comprising at least methanol as the oxygenate.

The ethane, propane, naphtha, and other hydrocarbons may be steam cracked in the hydrocarbon cracking unit 20 to produce at least ethylene. The hydrocarbon cracking unit 20 may be operated under conditions (i.e., temperature, pressure, gas hourly space velocity, etc.) sufficient to produce one or more light olefins, such as ethylene and propylene, from the hydrocarbons in the hydrocarbon feedstock 12. In some embodiments, the stream cracking unit may be operated at a temperature of from 500° C., to 850° C., from 500° C. to 810° C., from 550° C. to 850° C., from 550° C. to 810° C., from 600° C. to 850° C., or from 600° C. to 810° C. The temperature of the steam cracking unit may depend on the composition of the hydrocarbon feedstock 12 introduced to the steam cracking unit. Other suitable operating conditions for hydrocarbon cracking processes are well known in the art.

The cracker effluent 22 may include one or more cracking reaction products, such as, but not limited to, ethylene, propylene, butenes (e.g., 1-butene, trans-2-butene, cis-2-butene, isobutene), ethane, propane, other light hydrocarbons, or combinations of these. The cracker effluent 22 can also include hydrogen, CO, acetylene, methyl acetylene, propadiene, methane, other compounds produced in the hydrocarbon cracking unit 20, unreacted constituents of the hydrocarbon feedstock 12, or combinations of these. For example, the cracking reactions in the hydrocarbon cracking unit 20 may produce byproducts, such as hydrogen and CO, and side-reaction products, such as acetylene, methyl acetylene, propadiene, other side-reaction products, or combinations of these. Additionally, unreacted hydrocarbons and/or other constituents of the hydrocarbon feedstock 12 may pass through the hydrocarbon cracking unit 20 without undergoing reaction so that the cracker effluent 22 includes these unreacted constituents of the hydrocarbon feedstock 12. Acid gases may also be produced in the hydrocarbon cracking unit 20.

Referring still to FIG. 1, the cracker effluent 22 may be passed from the hydrocarbon cracking unit 20 to the quench unit 30 downstream of the hydrocarbon cracking unit 20. The quench unit 30 may be operable to quench the cracker effluent 22 to reduce the temperature of the cracker effluent 22 and remove steam and heavy hydrocarbon constituents to produce a quenched cracker effluent 32. Quenching the cracker effluent 22 in the quench section 30 may separate steam and heavy hydrocarbon constituents from the cracker effluent 22 (e.g., separate the steam and heavy hydrocarbons from the gas stream of the cracker effluent 22). The quench section 30 may include two or more quench units, such as an oil quench unit operable to remove heavy hydrocarbon constituents and a water quench to remove steam from the cracked effluent 22. The quenched cracker effluent 32 may be passed to the acid gas removal process 34 to remove acid gases from the quenched cracker effluent 32 to produce the cracked gas 36. The quenched cracker effluent 32 or the cracked gas 36 may be passed to one or more compressors (not shown) that further reduce the volume of gas before sending the cracked gas 36 to the separation system 40.

Referring to FIG. 1, the cracked gas 32 may be passed to the separation system 40, which is downstream of the quench section 30, acid gas removal processes 34, and compressors (not shown). The separation system 40 may be operable to produce at least the hydrogenation feed 42 and an acetylene-depleted stream 44 from the cracked gas 32. The separation system 40 may include one or a plurality of separation units. The separation system 40 may be any type of separation system operable to produce the hydrogenation feed 42 from the cracked gas 36. In some embodiments, the separation system 40 may include a distillation unit in which the cracked gas 36 may be separated into the hydrogenation feed 42 and he acetylene-depleted stream 44 by differences in boiling point temperatures of the constituents. In some embodiments, the separation system 40 may be a multiple stage distillation column. Separation of the constituents of the cracked gas 36 by difference in boiling point temperature may include initially cooling the cracked gas 36 to temperatures less than the boiling point temperatures of one or more constituents of the cracked gas 36. Thus, the separation system 40 may include a condenser operable to condense one or more constituents of the cracked gas 36 upstream of the distillation unit. The separation system 40 is not limited to a distillation process. It is understood that other methods and processes for producing the hydrogenation feed 42 from the cracked gas 36 are contemplated.

As previously discussed, the hydrogenation feed 42 may include at least 95% by weight of the acetylene from the cracked gas 36 passed to the separation system 40. The hydrogenation feed 42 may include saturated and unsaturated hydrocarbons, such as, but not limited to, ethylene ($C_2H_4$), propylene ($C_3H_6$), acetylene ($C_2H_2$), methyl acetylene ($H_3C-C\equiv CH$), propadiene ($HC=C=CH$), methane ($CH_4$), ethane ($C_2H_6$), propane ($C_3H_8$), or combinations of these. The hydrogenation feed 42 may also include non-hydrocarbon gases, such as, but not limited to, hydrogen, CO, carbon dioxide ($CO_2$), inert gases, or combinations of these. Inert gases may include nitrogen, argon, or other inert gases present in the olefin production system 10. In some embodiments, the hydrogenation feed 42 may include acetylene, hydrogen, carbon monoxide, and at least one product. The hydrogenation feed 42 may further include methyl acetylene, propadiene, or both. The product in the hydrogenation feed 42 may include one or more of ethylene, propylene, methane, ethane, propane, or combinations of these.

The acetylene-depleted stream 44 may include less than 5% by weight of the acetylene from the cracked gas 36. The acetylene-depleted stream 44 may include a greater weight percentage of higher boiling point hydrocarbons compared to the hydrogenation feed 42. These higher boiling point hydrocarbons may include saturated and unsaturated hydrocarbons, such as, but not limited to propane, propylene, butane, butenes, butadiene, pentane, or other higher boiling temperature hydrocarbons.

The separation system 40 may be a front end depropanizer (FEDP) or a front end de-ethanizer (FEDE). When the separation system 40 is an FEDP, the hydrogenation feed 42 may include $C_{3-}$ hydrocarbons and non-hydrocarbon gases. The $C_{3-}$ hydrocarbons may include, but are not limited to, methane, ethane, propane, ethylene, propylene, acetylene, methyl acetylene, propadiene, and combinations of these. The light gases in the hydrogenation feed 42 may include hydrogen, CO, carbon dioxide, nitrogen, or other non-hydrocarbon gases. When the separation system 40 is an FEDP, the acetylene-depleted stream 44 may include the $C_{4+}$ hydrocarbons, such as butane, butenes, butadiene, pentane, pentenes (i.e., one or more of the various isomers of pentene), and other $C_{4+}$ hydrocarbons. In some embodiments, the separation system 40 may be an FEDE, in which case, the greater portions of the propane and propylene may be in the acetylene-depleted stream 44 rather than in the hydrogenation feed 42. Further information on various front end configurations for acetylene hydrogenation in olefin production processes can be found in "Overview on C2 and C3 Selective Hydrogenation in Ethylene Plants" by Edgar L. Mohundro, 15$^{th}$ Ethylene Produces Conference, 2003 AICHE Spring National Meeting, New Orleans, La., the entire contents of which are incorporated herein by reference.

Referring again to FIG. 1, the hydrogenation feed 42 may be passed to the acetylene hydrogenation unit 50. The hydrogenation feed 42 may be contacted with a hydrogenation catalyst in the acetylene hydrogenation unit 50. Contacting the hydrogenation feed 42 with the hydrogenation catalyst may produce a hydrogenation effluent, which may include the constituents of the hydrogenation feed 42 and reaction products from the hydrogenation reaction. The contacting of the hydrogenation feed 42 with the hydrogenation catalyst may cause hydrogenation of at least a portion of the acetylene in the hydrogenation feed 42 to produce the hydrogenation effluent 52, which may have a reduced concentration of acetylene compared to the hydrogenation feed 42. The acetylene hydrogenation unit 50 may include one or a plurality of hydrogenation reactors, such as 1, 2, 3, or more than 3 hydrogenation reactors. In some embodiments, the acetylene hydrogenation unit 50 may include a plurality of hydrogenation reactors in series, such as a first hydrogenation reactor, a second hydrogenation reactor downstream of the first hydrogenation reactor, and optionally a third hydrogenation reactor downstream of the second hydrogenation reactor. Heat exchangers may be positioned between each of the plurality of hydrogenation reactors of the acetylene hydrogenation unit 50. The hydrogenation reactors of the acetylene hydrogenation unit 50 may be fixed bed reactors comprising a fixed bed of the hydrogenation catalyst. The hydrogenation reactors of the acetylene hydrogenation unit 50 may be vapor phase reactors operable to conduct the hydrogenation reaction through contact of the hydrogenation catalyst (a solid) with reactants in the vapor phase.

Although not depicted in the figures, the acetylene hydrogenation unit 50 may include one or a plurality of temperature sensors, pressure sensors, flow meters, or combinations of these for measuring the temperature, pressure, or gas flow rates at one or a plurality of positions in the acetylene hydrogenation unit 50. The temperature, pressure, and/or gas flow rate may be determined for one or more of the plurality of acetylene hydrogenation reactors of the acetylene hydrogenation unit 50 and/or for the hydrogenation feed 42 introduced to the acetylene hydrogenation unit 50. The method of operating the acetylene hydrogenation unit 50 may include determining the temperature of the acetylene hydrogenation unit 50, a temperature of the hydrogenation feed 42 passed to the acetylene hydrogenation unit 50, or both.

The acetylene hydrogenation unit 50 may also include one or a plurality of analyzers, such as GC analyzers, operable to measure the concentration of hydrogen in the hydrogenation feed 42, the hydrogenation effluent 52, intermediate effluents from one or more of the hydrogenation reactors of the acetylene hydrogenation unit 50, or combinations of these. In some embodiments, the stream for hydrogen concentration analysis may be retrieved from the hydrogenation feed 42 before introducing the hydrogenation feed 42 to the acetylene hydrogenation unit 50. Alternatively or additionally, the stream for hydrogen concentration analysis may be retrieved from the hydrogenation effluent 52 passed out of the acetylene hydrogenation unit 50. In some embodiments, the stream for hydrogen concentration analysis may be retrieved from one or more intermediate effluent streams passed of one of the hydrogenation reactors of the acetylene hydrogenation unit 50. The method of operating the acetylene hydrogenation unit 50 may include determining the concentration of hydrogen in the acetylene hydrogenation unit 50. Determining the concentration of hydrogen in the acetylene hydrogenation unit 50 may include measuring or analyzing the hydrogen concentration in the hydrogenation feed 42, the hydrogenation effluent 52, or both.

The hydrogenation catalyst may be an acetylene hydrogenation catalyst that is a catalyst selective for hydrogenating acetylene relative to product compounds in the hydrogenation feed 42. The hydrogenation catalyst may be any known catalyst for selectively hydrogenating acetylene. Commercial catalysts for acetylene hydrogenation are widely available, and the present disclosure is not limited to any specific composition recited herein.

The acetylene hydrogenation unit 50 can be operated at conditions under which the catalytic hydrogenation is selective for hydrogenation of acetylene over hydrogenation of propylene and ethylene. The acetylene hydrogenation unit 50 may be operated at a temperature sufficient to hydrogenate acetylene at a conversion rate that prevents breakthrough of acetylene to downstream processes, but less than a temperature resulting in increased hydrogenation of olefins and thermal runaway of the acetylene hydrogenation unit 50. The operating temperature of the acetylene hydrogenation unit 50 may be from 10° C. to 200° C., such as from 10° C. to 100° C., although the operating temperature of the acetylene hydrogenation unit 50 may depend on the composition of the hydrogenation feed 42, as will be described in further detail herein. Other factors influencing the operating temperature of the acetylene hydrogenation unit 50 may include, but are not limited to, the type of hydrogenation catalyst, the age/activity of the hydrogenation catalyst, flow rate, inlet acetylene concentration, CO concentration, presence of contaminants or poisons, other factors, or combinations of these. The acetylene hydrogenation unit 50 may operate at a pressure of from 100 pounds per square inch gauge (psig) to 1000 psig (i.e., about 690 kilopascals (kPa) to about 6900 kPa). The acetylene hydrogenation unit 50 may additionally operate at a gas hourly space velocity (GHSV) of from 1,000 to 14,000 (volume per volume of catalyst per hour).

The hydrogenation effluent 52 may refer to the effluents or compositions passed out of the acetylene hydrogenation unit 50, such as out of the last hydrogenation reactor of the acetylene hydrogenation unit 50. The hydrogenation effluent 52 may have an acetylene concentration less than the acetylene concentration of the hydrogenation feed 42. The hydrogenation effluent 52 may have an acetylene concentration of less than or equal to a threshold concentration, which may be specified by the olefin product user. In some embodiments, the hydrogenation effluent 52 may have an acetylene concentration of less than or equal to 2 part per million by volume (ppmv), less than or equal to 1 ppmv, less than or equal to 0.5 ppmv, or even less than or equal to 0.1 ppmv. The hydrogenation reaction in the acetylene hydrogenation unit 50 may consume hydrogen from the hydrogenation feed 42, but the change in concentration of hydrogen in the hydrogenation effluent 52 compared to the hydrogenation feed 42 may be less than the detection limits of analytical instruments due to the small concentrations of acetylene in the hydrogenation feed 42 (e.g., in the parts per million range). The hydrogenation catalyst and operating conditions of the acetylene hydrogenation unit 50 may be selective for hydrogenating acetylene relative to hydrogenation of product compounds, such as propylene and ethylene, produced in the hydrocarbon cracking unit 20.

Figure 5:
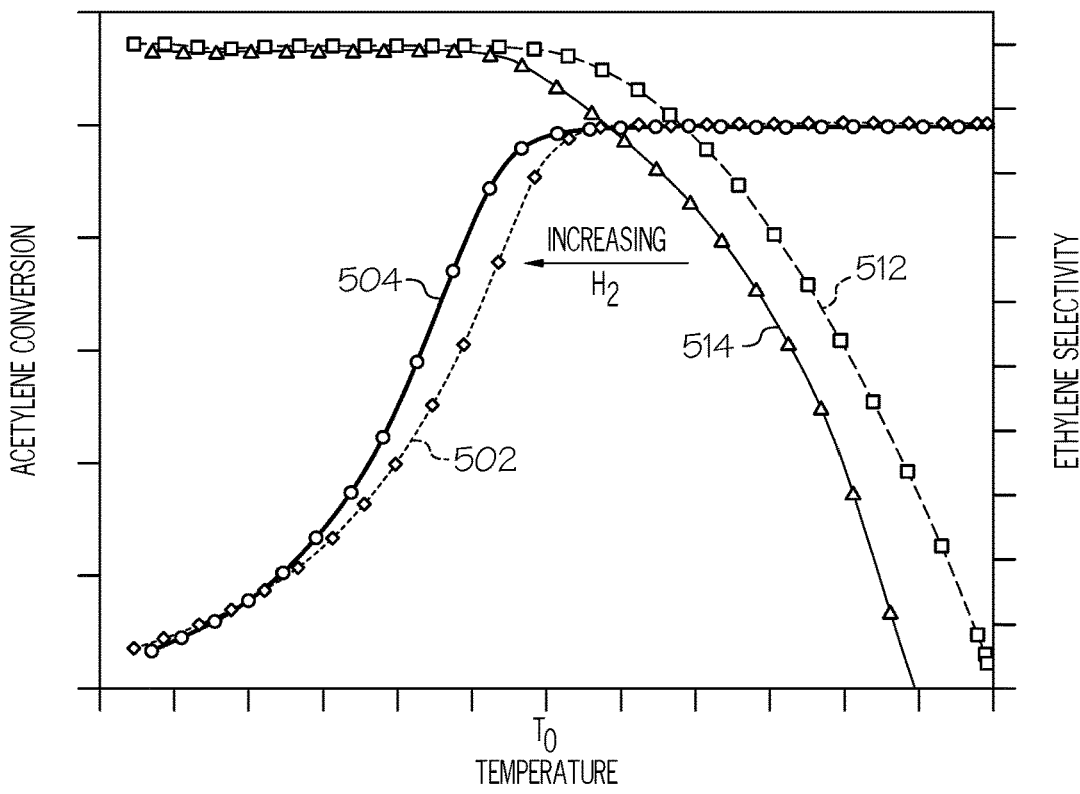
FIG. 5 graphically depicts a conversion of acetylene (y-axis-left) and ethylene selectivity (y-axis-right) of the acetylene hydrogenation unit as a function of temperature at two different hydrogen concentrations, according to one or more embodiments described herein.

Variations in the hydrogen concentration in the hydrogenation feed 42 can influence the acetylene conversion and ethylene selectivity of the acetylene hydrogenation unit 50. Referring to FIG. 5, the acetylene conversion as a function of inlet temperature of the hydrogenation feed 42 to the acetylene hydrogenation unit 50 is graphically depicted for a hydrogenation feed having 18 mol % hydrogen (curve 502) and for a hydrogenation feed having 28 mol % hydrogen (curve 504). As shown in FIG. 5, increasing the hydrogen concentration from 18 mol % (502) to 28 mol % (504) shifts the acetylene conversion curve towards lesser reactor temperatures for achieving the same acetylene conversion. Not intending to be bound by theory, it is believed that since hydrogen is a reactant in the hydrogenation reaction, increasing the concentration of hydrogen increases the probability of reaction between the hydrogen and the acetylene. As shown in FIG. 5, an inlet temperature of the hydrogenation feed required to produce a specific acetylene conversion for a hydrogen concentration of 28% will be less than the inlet temperature required to achieve the specific acetylene conversion for the hydrogenation feed having a hydrogen concentration of 18%. Increasing the hydrogen concentration also increases the probability of reaction between hydrogen and other unsaturated constituents, such as propadiene and/or methyl acetylene, as well as product olefins like ethylene and propylene.

FIG. 5 also graphically depicts the ethylene selectivity as a function of inlet temperature of the hydrogenation feed 42 to the acetylene hydrogenation unit 50 for a hydrogenation feed having 18 mol % hydrogen (curve 512) and for a hydrogenation feed having 28 mol % hydrogen (curve 514). In FIG. 5, temperature $T_0$ on the x-axis is a temperature of the hydrogenation feed 42 above which the ethylene selectivity begins to decrease. As shown in FIG. 5, increasing the hydrogen concentration from 18 mol % (512) to 28 mol % (514) shifts the ethylene selectivity curve towards lower reactor temperatures, which indicates that the temperature at which ethylene hydrogenation occurs decreases with increasing hydrogen concentration. If operated at the same inlet temperature of the hydrogenation feed of greater than $T_0$, the ethylene selectivity may be about 20% less for the hydrogenation feed having 28% hydrogen compared to the hydrogenation feed having 18% hydrogen. Thus, an increase in the hydrogen concentration at a constant inlet temperature may cause an increase in hydrogenation of ethylene and other product olefins, resulting in value loss. Increased olefin hydrogenation may also lead to thermal runaway of the acetylene hydrogenation unit 50. As shown in FIG. 5, increasing or decreasing the hydrogen concentration in the hydrogenation feed 42 or the acetylene hydrogenation unit 50 can influence the process operating window with respect to both acetylene conversion and ethylene selectivity as a function of temperature.

Thus, FIG. 5 demonstrates that increasing the hydrogen concentration in the acetylene hydrogenation unit 50 may increase the acetylene conversion and decreases the ethylene selectivity at a given inlet temperature of the hydrogenation feed 42.

Figure 6:
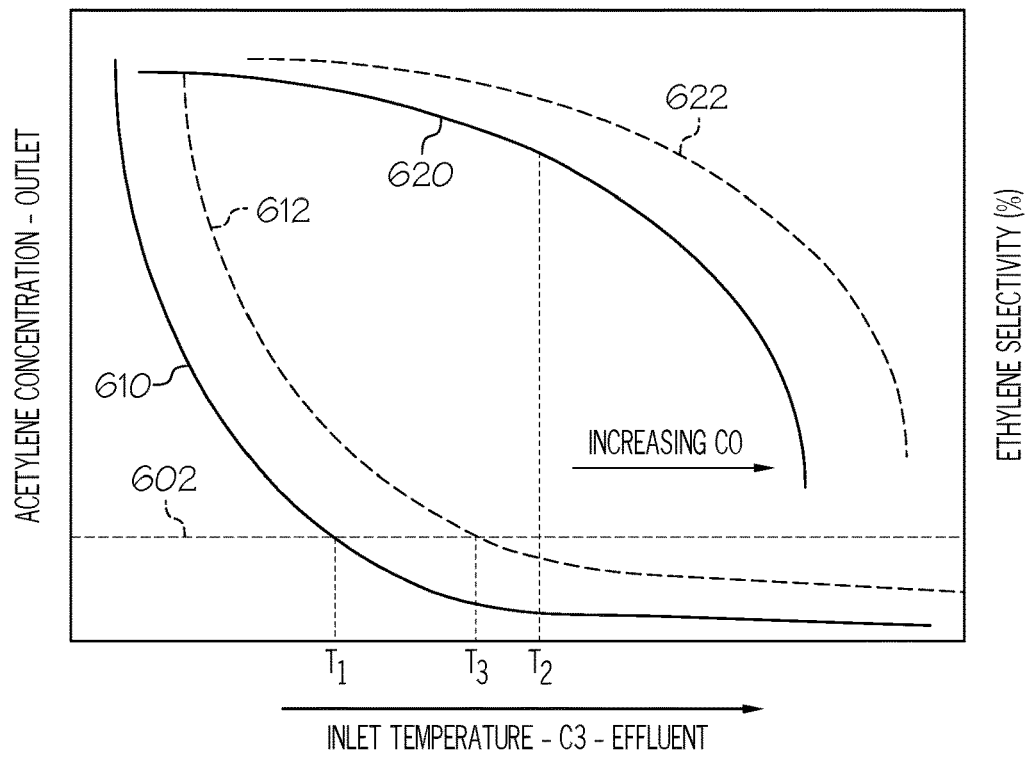
FIG. 6 graphically depicts a concentration of acetylene (y-axis-left) and ethylene selectivity (y-axis-right) for the acetylene hydrogenation unit as a function of a temperature (x-axis) of a hydrogenation feed passed to the acetylene hydrogenation unit, according to one or more embodiments described herein.

Referring now to FIG. 6, the acetylene concentration in the hydrogenation effluent 52 (y-axis left) and the ethylene selectivity of the acetylene hydrogenation unit 50 (y-axis right) are depicted as functions of the temperature (x-axis) of the hydrogenation feed 42 at the inlet to the acetylene hydrogenation unit 50. Line 602 in FIG. 6 represents a target acetylene concentration for the hydrogenation effluent 52, below which the concentration the acetylene is considered reduced to a level sufficient to meet product specifications. As shown in FIG. 6, the acetylene concentration (curve 610) in the hydrogenation effluent 52 decreases with increasing inlet temperature for a given composition of the hydrogenation feed 42. FIG. 6 shows that the acetylene concentration 610 in the hydrogenation effluent 52 can be increased or decreased by decreasing or increasing, respectively, the inlet temperature to the acetylene hydrogenation unit 50. Temperature $T_1$ for the given composition of the hydrogenation feed 42 for curve 610 can be defined as the lowest temperature at which the acetylene concentration in the hydrogenation effluent 52 is equal to or less than the target acetylene concentration 602. At temperatures of the hydrogenation feed 42 greater than $T_1$ the acetylene concentration (610) in the hydrogenation effluent 52 is less than the target acetylene concentration. For temperatures of the hydrogenation feed 42 less than $T_1$, the acetylene concentration (610) in the hydrogenation effluent 52 may be greater than the target acetylene concentration. At temperatures less than T1, the greater concentration of acetylene in the hydrogenation effluent 52 may lead to breakthrough of acetylene to downstream processes.

FIG. 6 shows the ethylene selectivity of the acetylene hydrogenation unit 50 (curve 620) as a function of inlet temperature for the same composition of the hydrogenation feed 42 as curve 610. As shown in FIG. 6, the ethylene selectivity (curve 620) decreases with increasing inlet temperature. Thus, as the inlet temperature to the acetylene hydrogenation unit 50 increases, the ethylene selectivity of the acetylene hydrogenation unit 50 decreases, indicating a reduction in the concentration of ethylene in the hydrogenation effluent 52, which may be caused by increased hydrogenation of ethylene in the acetylene hydrogenation unit 50. Increased hydrogenation of ethylene may lead to thermal runaway. For example, at temperatures of the hydrogenation feed 42 greater than about $T_2$, the ethylene selectivity may decrease to a point at which an unacceptable amount of ethylene undergoes hydrogenation. Since the ethylene hydrogenation reaction is exothermic, additional heat from the increased hydrogenation of ethylene and other olefins is released and may further increase the temperature in the acetylene hydrogenation unit 50, which further increases the reaction rate for hydrogenation of ethylene and propylene. The increasing heat generated from increasing hydrogenation of ethylene and other olefins may lead to thermal runaway of the acetylene hydrogenation unit 50. Thermal runaway can result in increased loss of olefin products through over-hydrogenation of the ethylene and propylene. Additionally, the increased temperatures in excess of 200° C. experienced during thermal runaway can damage the hydrogenation catalyst and equipment, such as reactors, instruments, heat exchangers, and other equipment, and may increase safety risks.

Referring again to FIG. 6, an operating window for the inlet temperature of the hydrogenation feed 42 introduced to the acetylene hydrogenation unit 50 for a given composition of the hydrogenation feed 42 can be defined between the inlet temperature $T_1$, below which the acetylene concentration in the hydrogenation effluent 52 is greater than the target acetylene concentration 602, and the inlet temperature $T_2$, above which the ethylene selectivity decreases and hydrogenation of olefin products can result in thermal runaway of the acetylene hydrogenation unit 50.

Referring again to FIG. 6, the process window for operation of the acetylene hydrogenation unit 50 may be modified or shifted by changes in the CO concentration, the hydrogen concentration, or both in the acetylene hydrogenation unit 50. Increasing the CO concentration in the acetylene hydrogenation unit 50 may widen the process window and shift the process window for the temperature of the hydrogenation feed 42 towards greater temperatures. In FIG. 6, curve 612 represents the acetylene concentration in the hydrogenation effluent 52 as a function of inlet temperature of the hydrogenation feed 42 for operation of the acetylene hydrogenation unit 50 with an increased concentration of CO compared to the concentration of CO for curve 610. By increasing the concentration of CO in the acetylene hydrogenation unit 50, the inlet temperature $T_3$ of the hydrogenation feed 42 at which the acetylene concentration in the hydrogenation effluent 52 is equal to the target acetylene concentration 602 is greater than the corresponding temperature $T_1$ of the hydrogenation feed 42 for curve 610 (having a lesser concentration of CO).

Increasing the CO concentration in the acetylene hydrogenation unit 50 may also shift the ethylene selectivity curve towards greater inlet temperatures. Curve 622 represents the ethylene selectivity for the acetylene hydrogenation unit 50 as a function of time for a greater CO concentration compared to curve 620. As shown in FIG. 6, increasing the CO concentration (curve 622) in the acetylene hydrogenation unit 50 can enable operation of the acetylene hydrogenation unit 50 at greater inlet temperatures compared to operating the acetylene hydrogenation unit 50 with a lesser concentration of CO. Thus, increasing the CO concentration in the acetylene hydrogenation unit 50 can enable operation of the acetylene hydrogenation unit 50 at a greater temperature without causing thermal runaway.

As previously discussed, the hydrogen concentration in the hydrogenation feed 42 (and acetylene hydrogenation unit 50) may increase or decrease based on operation of the upstream hydrocarbon cracking unit 20 and the composition of the hydrocarbon feedstock 12 introduced to the hydrocarbon cracking unit 20. The following Table 1 provides the mole percentages (mol %) of hydrogen in cracking effluent streams produced from cracking ethane, propane, and naphtha, based on estimates generated using chemical process simulation software. As shown by Table 1, cracking ethane produces a greater concentration of hydrogen compared to cracking propane and naphtha. Thus, introducing a hydrocarbon feedstock 12 feedstock having an increased concentration of ethane will increase the hydrogen concentration in the cracker effluent 22 as well as the concentration of hydrogen in the hydrogenation feed 42 passed from the separation system 40 to the acetylene hydrogenation unit 50.

TABLE 1

| Hydrocarbon | Hydrogen Concentration in Cracker Effluent 22 (mol %) |
|---|---|
| Ethane | 37 |
| Propane | 17 |
| Naphtha | 13 |

In an acetylene hydrogenation unit 50 under operation conditions selected for a specific hydrogen concentration (e.g. at constant inlet temperature of acetylene reactor), sudden increases in the hydrogen concentration of the hydrogenation feed 42 resulting from fast switching to use of lighter feedstocks to the olefin process may result in excessive hydrogenation of product olefins and thermal runaway of the acetylene hydrogenation unit 50. Decreases in the hydrogen concentration in the hydrogenation feed 42 from fast switching to use of heavier feedstocks may lead to reduced conversion of acetylene and acetylene breakthrough to downstream processes if the other operation conditions are not altered.

Figure 2:
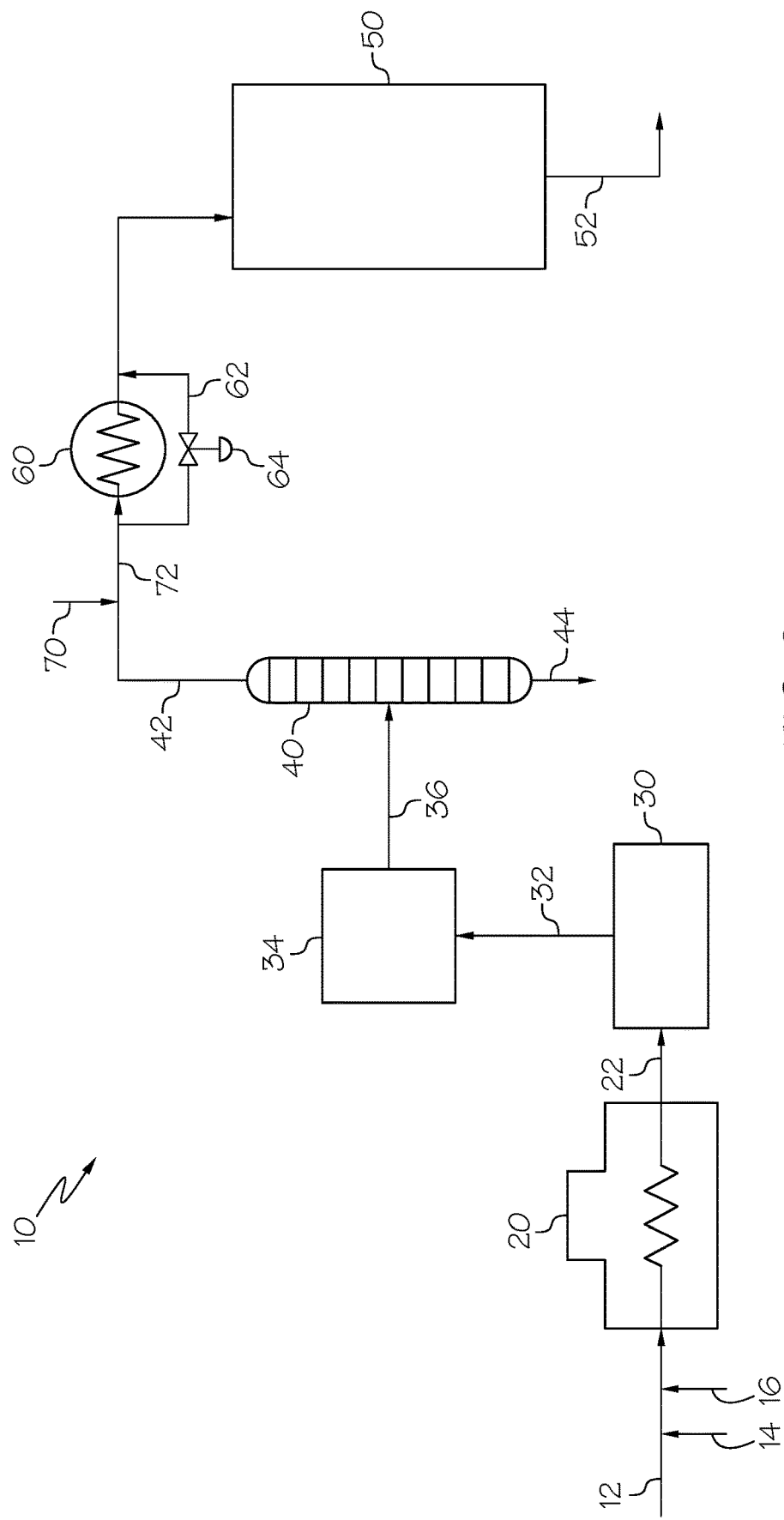
FIG. 2 schematically depicts the process for producing olefins of FIG. 1 in which supplemental CO is added to a hydrogenation feed upstream of the acetylene hydrogenation unit, according to one or more embodiments shown and described herein.
Figure 3:
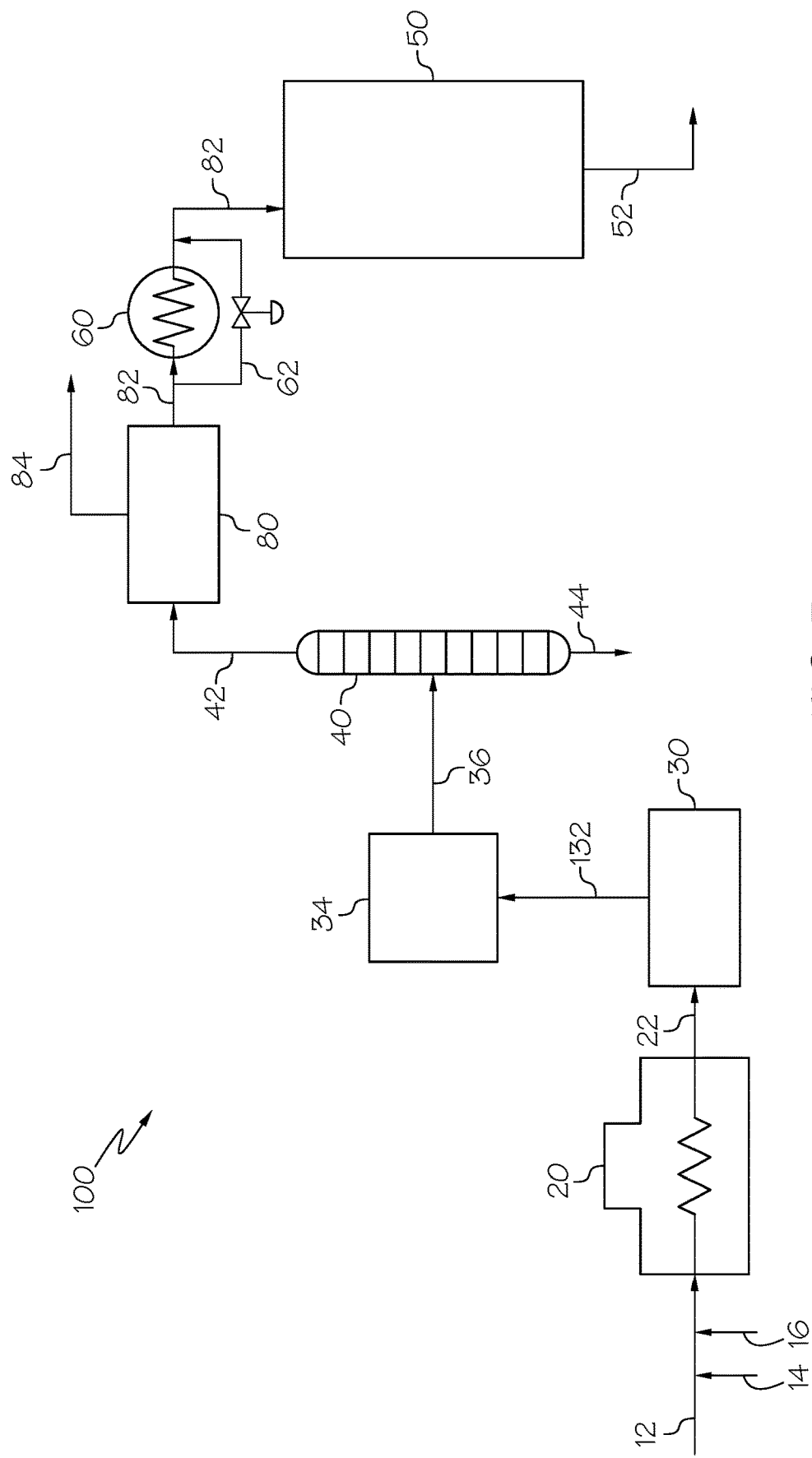
FIG. 3 schematically depicts another process for producing olefins, the process including a hydrogen separation system upstream of an acetylene hydrogenation unit, according to one or more embodiment described herein.

Referring to FIGS. 1-2, the methods disclosed herein for operating the acetylene hydrogenation unit 50 may provide a fast adjustment of operation conditions for the acetylene hydrogenation unit 50 based on a determination of the concentration of hydrogen in the acetylene hydrogenation unit 50 (e.g., hydrogen concentration in the hydrogenation feed 42, hydrogenation effluent 52, and/or any intermediate effluent or stream in the acetylene hydrogenation unit 50). The operation of the acetylene hydrogenation unit 50 may be adjusted by increasing or decreasing the temperature of the acetylene hydrogenation unit 50, the concentration of CO in the acetylene hydrogenation unit 50, or combinations of these. The temperature of the acetylene hydrogenation unit 50 may be increased or decreased by increasing or decreasing a temperature of the hydrogenation feed 42. The temperature of the hydrogenation feed 42 may be increased or decreased prior to passing the hydrogenation feed 42 to the acetylene hydrogenation unit 50. The concentration of CO in the acetylene hydrogenation unit 50 may be increased or decreased by increasing or decreasing the CO concentration in the hydrogenation feed 42. In some embodiments, the method may include increasing or decreasing the concentration of hydrogen in the hydrogenation feed 42, as shown in FIG. 3.

Referring again to FIG. 1, the method of operating the acetylene hydrogenation unit 50 may include determining the hydrogen concentration in the acetylene hydrogenation unit 50 and increasing or decreasing a temperature of the acetylene hydrogenation unit 50, a concentration of CO in the acetylene hydrogenation unit 50, or both, based on the determination of the hydrogen concentration in the acetylene hydrogenation unit 50.

The hydrogen concentration in the acetylene hydrogenation unit 50 may be determined by measuring the concentration of hydrogen in the hydrogenation feed 42, the hydrogenation effluent 52, or both, using one or a plurality of analyzers, as previously discussed herein. Alternatively or additionally, the hydrogen concentration in the acetylene hydrogenation unit 50, may be extrapolated by measuring the composition, including the concentration of hydrogen, at one or more locations upstream of the acetylene hydrogenation unit 50, such as the hydrocarbon cracking unit 20, the cracker effluent 22, the quench unit 30, the quenched cracker effluent 32, the acid gas removal processes 34, the cracked gas 36, the separation system 40, or combinations of these. The hydrogen concentration in the acetylene hydrogenation unit 50 may also be determined by determining the composition of the hydrocarbon feedstock 12 and calculating the hydrogen concentration from the hydrocarbon feedstock 12 and operating conditions of the hydrocarbon cracking unit 20 and, optionally, the quench unit 30, acid gas removal processes 34, and/or the separation system 40. Other methods and techniques for determining the hydrogen concentration in the acetylene hydrogenation unit 50, are contemplated.

Referring again to FIG. 1, the method of operating the acetylene hydrogenation unit 50 in response to changes in the hydrogen concentration of the hydrogenation feed 42 may include determining the hydrogen concentration of the acetylene hydrogenation unit 50 and increasing or decreasing the temperature of the acetylene hydrogenation unit 50 based on the determination of the hydrogen concentration in the hydrogenation unit 50. The method may further include determining the temperature of the acetylene hydrogenation unit 50, the inlet temperature of the hydrogenation feed 42, or both. The temperature of the hydrogenation feed 42 at the inlet of acetylene hydrogenation unit 50 may be controlled by controlling the amount of feed going through the heat exchanger 60 and the heat exchanger bypass 62. In some embodiments, the temperature of the acetylene hydrogenation unit 50 may be determined by measuring the temperature with one or more temperature sensors known in the art for measuring the temperature of an interior reaction zone of a reactor.

Referring to FIG. 1, in some embodiments, the temperature of the acetylene hydrogenation unit 50 may be increased or decreased by increasing or decreasing, respectively, the temperature of the hydrogenation feed 42. The method for operating the acetylene hydrogenation unit 50 may include increasing or decreasing the temperature of the hydrogenation feed 42 at the inlet of the acetylene hydrogenation unit 50 based on the determination of the hydrogen concentration in the acetylene hydrogenation unit 50. For each incremental change in the hydrogen concentration in the hydrogenation feed 42 or the acetylene hydrogenation unit 50, the temperature of the hydrogenation feed 42 at the inlet to the acetylene hydrogenation unit 50 may be increased or decreased by a magnitude sufficient to maintain the acetylene concentration in the hydrogenation effluent 52 below the target acetylene concentration or to reduce hydrogenation of propylene and/or ethylene and prevent thermal runaway of the acetylene hydrogenation unit 50. The temperature of the hydrogenation feed 42 at the inlet to the acetylene hydrogenation unit 50 may be decreased in response to an increase in the hydrogen concentration and increased in response to a decrease in hydrogen concentration. In some embodiments, the inlet temperature of the hydrogenation feed 42 may be decreased by from 0.5° C. to 2.0° C., or from 0.5° C. to 1.5° C., or even from 0.5° C. to 1.0° C. for each incremental increase of 5 volume percent (vol. %) in the hydrogen concentration in the hydrogenation feed 42 or the acetylene hydrogenation unit 50 and increased by from 0.5° C. to 2.0° C., or from 0.5° C. to 1.5° C., or even from 0.5° C. to 1.0° C. for each incremental decrease of 5 vol. % in the hydrogen concentration in the hydrogenation feed 42 the acetylene hydrogenation unit 50 of 5 vol. %. The increase of 5 vol. % and decrease of 5 vol. % in the hydrogen concentration in the hydrogenation feed 42 refer to the absolute increase and absolute decrease, respectively, in the volume percent (vol. %) of hydrogen based on the total volume flow rate of the hydrogenation feed 42. For example, a change in the vol. % of hydrogen in the hydrogenation feed 42 from 20 vol. % to 25 vol. % would be an increase in the hydrogen concentration of 5 vol. %.

Referring to FIG. 1, the olefin production process 10 may include a heat exchanger 60 disposed between the separation system 40 and the acetylene hydrogenation unit 50. The heat exchanger 60 may include the bypass 62 having a control valve 64. The temperature of the hydrogenation feed 42 at the inlet of the acetylene hydrogenation unit 50 may be increased or decreased by controlling the amount of the hydrogenation feed 42 passing through the heat exchanger 60 and the amount of the hydrogenation feed 42 bypassing the heat exchanger 60 through the bypass 62. Controlling an amount of the hydrogenation feed 42 bypassed around the heat exchanger 60 may allow for increasing or decreasing the temperature of the hydrogenation feed 42 at the inlet of the acetylene hydrogenation unit 50. The heat exchanger 60 for the hydrogenation feed 42 may be any type of heat exchanger known in the chemical industry. In some embodiments, the method of operating the acetylene hydrogenation unit 50 may include determining a hydrogen concentration in the hydrogenation feed 42, increasing a temperature of the hydrogenation feed 42 in response to a decrease in the hydrogen concentration of the hydrogenation feed 42, and decreasing a temperature of the hydrogenation feed 42 in response to an increase in the hydrogen concentration in the hydrogenation feed 42.

In some embodiments, increasing the temperature of the acetylene hydrogenation unit 50 may include increasing or decreasing the acetylene hydrogenation unit 50 directly based on the hydrogen concentration in the acetylene hydrogenation unit 50 through heat exchange with the acetylene hydrogenation unit 50 itself, such as by active cooling or heating the acetylene hydrogenation unit 50, or one or more of the hydrogenation reactors thereof. Any suitable means of exchanging heat with the hydrogenation reactors of the acetylene hydrogenation unit 50 may be used to change the temperature of the acetylene hydrogenation unit 50. Examples may include, but are not limited to, increasing/decreasing the temperature of the heating media for isothermal operation of acetylene reactors with tube-in-the-shell design, or for adiabatic operation, jacketing the hydrogenation reactors, passing intermediate streams through heat exchangers, or other methods of exchanging heat with the acetylene hydrogenation unit 50.

Referring to FIG. 1, the method of operating the acetylene hydrogenation unit 50 in response to changes in the hydrogen concentration may include determining the hydrogen concentration of the acetylene hydrogenation unit 50 and increasing or decreasing the concentration of CO in the hydrogenation feed 42. As previously discussed, increasing or decreasing the CO concentration in the hydrogenation feed 42 in response to the hydrogen concentration may shift the process window of the acetylene hydrogenation unit 50. The method may further include increasing or decreasing the temperature of the hydrogenation feed 42 in conjunction with changing the CO concentration of the hydrogenation feed 42.

The method may further include determining the CO concentration in the acetylene hydrogenation unit 50. Determining the CO concentration in the acetylene hydrogenation unit 50 may include measuring the CO concentration in the hydrogenation feed 42, the hydrogenation effluent 52, or both. The CO concentration may be measured in these streams using an analyzer, such as a GC analyzer, as described previously in relation to measuring the hydrogen concentrations. It is noted that CO is not consumed in the hydrogenation reaction of acetylene; however, some CO may be consumed through side reactions that may occur within the acetylene hydrogenation unit 50. The amount of CO consumed by side reactions may be less than 1 wt. %. At least 99 wt. % of the CO in the hydrogenation feed 42 may pass into and through the acetylene hydrogenation unit 50. Alternatively or additionally, the CO concentration in the acetylene hydrogenation unit 50 or the hydrogenation feed 42 may be determined by extrapolating the concentration of CO in one or more of the hydrocarbon cracking unit 20, the cracker effluent 22, the quench unit 30, the quenched cracker effluent 32, the acid gas removal processes 34, the cracked gas 36, the separation system 40, or combinations of these. The concentration of CO in any streams or effluents upstream of the separation system 40 can be used to calculate the CO in the hydrogenation feed 42 using mass balance calculations for one or more of the quench unit 30, acid gas removal processes 34, and separation system 40. Other methods and techniques for determining the CO concentration in the acetylene hydrogenation unit 50 or the hydrogenation feed 42 are contemplated.

The CO concentration in the acetylene hydrogenation unit 50 (e.g., CO concentration in the hydrogenation feed 42) may be increased in response to an increase in the hydrogen concentration and decreased in response to a decrease in hydrogen concentration. In some embodiments, the CO concentration of the acetylene hydrogenation unit 50 or the hydrogenation feed 42 may be increased by at least 10 part per million by volume (ppmv), by at least 15 ppmv, or by at least 20 ppmv, for each incremental increase of 5 vol. % in the hydrogen concentration in the acetylene hydrogenation unit 50 or the hydrogenation feed 42. Similarly, the CO concentration in the acetylene hydrogenation unit 50 or hydrogenation feed 42 may be decreased by at least 10 ppmv, by at least 15 ppmv, or at least 20 ppmv, for each incremental decrease of 5 vol. % in the hydrogen concentration in the acetylene hydrogenation unit 50 or the hydrogenation feed 42. As previously discussed, increasing or decreasing the CO concentration in the acetylene hydrogenation unit 50 or hydrogenation feed 42 may be accompanied by increasing or decreasing the temperature of the hydrogenation feed 42 to position the operating conditions of the acetylene hydrogenation unit 50 within the process window corresponding to the modified CO concentration.

In some embodiments, the CO concentration in the hydrogenation feed 42 or the acetylene hydrogenation unit 50 can be increased or decreased by increasing or decreasing the amount of CO produced in the hydrocarbon cracking unit 20. The amount of CO produced in the hydrocarbon cracking unit 20 may be increased or decreased by changing one or more operating parameters of the hydrocarbon cracking unit 20. In some embodiments, the amount of CO produced in a steam cracking unit may be modified by changing the amount of sulfur-containing compounds, oxygenates such as methanol, or both, introduced to the steam cracking unit. In some embodiments, the concentration of CO in the cracker effluent 22, can be increased or decreased by decreasing or increasing, respectively, the amount of sulfur-containing compounds introduced to the hydrocarbon cracking unit 20. Sulfur-containing compounds may include, but are not limited to, one or more of dimethyl disulfide (DMDS), dimethyl sulfide (DMS), diethyl disulfide (DES), methyl mercaptan (MM), or combination thereof. The amount of sulfur-containing compounds introduced to the hydrocarbon cracking unit 20 may be increased or decreased by increasing or decreasing the flow rate of sulfur-containing compounds 14 combined with the hydrocarbon feedstock 12 upstream of the hydrocarbon cracking unit 20. Increasing the sulfur introduced to the hydrocarbon cracking unit 20 may passivate the heating coils in the cracking furnace, thereby controlling the amount of coke formed in the hydrocarbon cracking unit 20. Although normally added to the hydrocarbon cracking unit 20 as an anti-freezing agent, the amount of methanol introduced to the hydrocarbon cracking unit 20 may also influence the amount of CO produced in the hydrocarbon cracking unit 20.

Referring to FIG. 2, in some embodiments, the CO concentration in the acetylene hydrogenation unit 50 may be increased or decreased by increasing or decreasing, respectively, the CO concentration of the hydrogenation feed 42. In some embodiments, increasing the concentration of CO in the acetylene hydrogenation unit 50 may include combining the hydrogenation feed 42 with a CO-containing composition 70 to produce a mixed acetylene-containing composition 72 that includes CO and passing the mixed acetylene-containing composition 72 to the acetylene hydrogenation unit 50. The CO-containing composition 70 may be CO gas or a combination of CO with one or more other gases, such as nitrogen or other inert gases. The CO concentration of the mixed hydrogenation feed 72 may be greater than the CO concentration in the hydrogenation feed 42. The CO concentration in the acetylene hydrogenation unit 50 may be increased or decreased by increasing or decreasing, respectively, a proportion of the CO-containing composition 70 relative to the hydrogenation feed 42 in the mixed acetylene-containing composition 72 based on the determination of the hydrogen concentration in the hydrogenation feed 42 or the acetylene hydrogenation unit 50. It is noted that the hydrogen concentration, the CO concentration, or both may be determined by measuring the concentrations of these constituents in the mixed hydrogenation feed 72 in addition to or instead of measuring the concentrations of hydrogen and CO in the hydrogenation feed 42 or the hydrogenation effluent 52. As previously discussed, adjusting the composition of CO in acetylene hydrogenation unit 50 by combining the CO-containing composition 70 with the hydrogenation feed 42 may be accompanied by an adjustment to the temperature of the hydrogenation feed 42 or the mixed hydrogenation feed 72 (e.g., as shown in FIG. 2).

Referring now to FIG. 3, in some embodiments, the method of operating the acetylene hydrogenation unit 50 may include decreasing the concentration of hydrogen in the hydrogenation feed 42 to produce a reduced-hydrogen hydrogenation feed 82 and passing the reduced-hydrogen hydrogenation feed 82 to the acetylene hydrogenation unit 50. Reducing the hydrogen concentration in the hydrogenation feed 42 may be accompanied by a corresponding change in the temperature of the reduced-hydrogen hydrogenation feed 82 prior to passing it to the acetylene hydrogenation unit 50. The hydrogen concentration in the hydrogenation feed 42 may be reduced by passing the hydrogenation feed 42 to a hydrogen separation system 80 operable to remove at least a portion of the hydrogen from the hydrogenation feed 42 to produce the reduced hydrogen hydrogenation feed 82 and a hydrogen stream 84. The hydrogen separation system 80 may be any type of process or unit operation capable of reducing the hydrogen concentration of the hydrogenation feed 42. Unit operations for reducing the hydrogen concentration of the hydrogenation feed 42 may include, but are not limited to, pressure swing adsorption processes, or other separation processes. The concentration of hydrogen in the reduced-hydrogen hydrogenation feed 82 may be increased or decreased by modifying the operating conditions of the hydrogen separation system 80 or by combining at least a portion of the hydrogen stream 84 with the reduced-hydrogen hydrogenation feed 82. Modifying the hydrogen concentration in the hydrogenation feed 42 may be accompanied by a corresponding increase or decrease in the temperature of the reduced-hydrogen hydrogenation feed 82 passed to the acetylene hydrogenation unit 50.

The methods disclosed herein for operating the acetylene hydrogenation unit 50 may include any combination of one or more of adjusting the temperature of the hydrogenation feed 42 at the reactor inlet, adjusting the temperature of the acetylene hydrogenation unit 50, adjusting the CO concentration in the hydrogenation feed 42, or adjusting the concentration of hydrogen in the hydrogenation feed 42, in response to changes in the hydrogen concentration in the acetylene hydrogenation unit 50. Referring to FIG. 1, in some embodiments, the methods of operating the acetylene hydrogenation unit 50 may include changing the temperature of the hydrogenation feed 42 at reactor inlet and changing the CO concentration in the hydrogenation feed 42 in response to changes in the hydrogen concentration of the hydrogenation feed 42.

In some embodiments, the methods of operating the acetylene hydrogenation unit 50 to modify the temperature of the acetylene hydrogenation unit 50, the CO concentration in the acetylene hydrogenation unit 50, or both in response to changes in the hydrogen concentration in the acetylene hydrogenation unit 50 may ensure that the acetylene concentration in the hydrogenation effluent 52 is less than the target acetylene concentration to reduce or prevent breakthrough of acetylene to downstream processes. The acetylene concentration of the hydrogenation effluent 52 passed out of the acetylene hydrogenation unit 50 may be less than or equal to 2 ppm by volume (ppmv), such as less than or equal to 1 ppmv, less than or equal to 0.5 ppmv, or even less than or equal to 0.1 ppmv. Additionally, the methods of operating the acetylene hydrogenation unit 50 to modify the temperature of the acetylene hydrogenation unit 50, the CO concentration in the acetylene hydrogenation unit 50, or both in response to changes in the hydrogen concentration in the acetylene hydrogenation unit 50 may reduce or prevent thermal runaway, which may cause a reduction in the yield of olefin products such as propylene and ethylene and may cause damage to catalysts and equipment caused by high temperatures resulting from thermal runaway.

The hydrogenation effluent 52 may be passed to one or more unit operations and processes downstream of the acetylene hydrogenation unit 50 for further processing of the hydrogenation effluent 52. Downstream processes may include vapor compression, separation, drying, or other operations and processes. The unit operations and processes downstream of the acetylene hydrogenation unit 50 may, ultimately, separate the hydrogenation effluent 52 into a plurality of gaseous streams, such as, but not limited to, an ethylene product stream, a propylene product stream, a propane stream, an ethane stream, other streams, or combinations of these streams. One or more of these product streams may be passed as reactants or raw materials to further production processes, such as polymer production processes.

Figure 4:
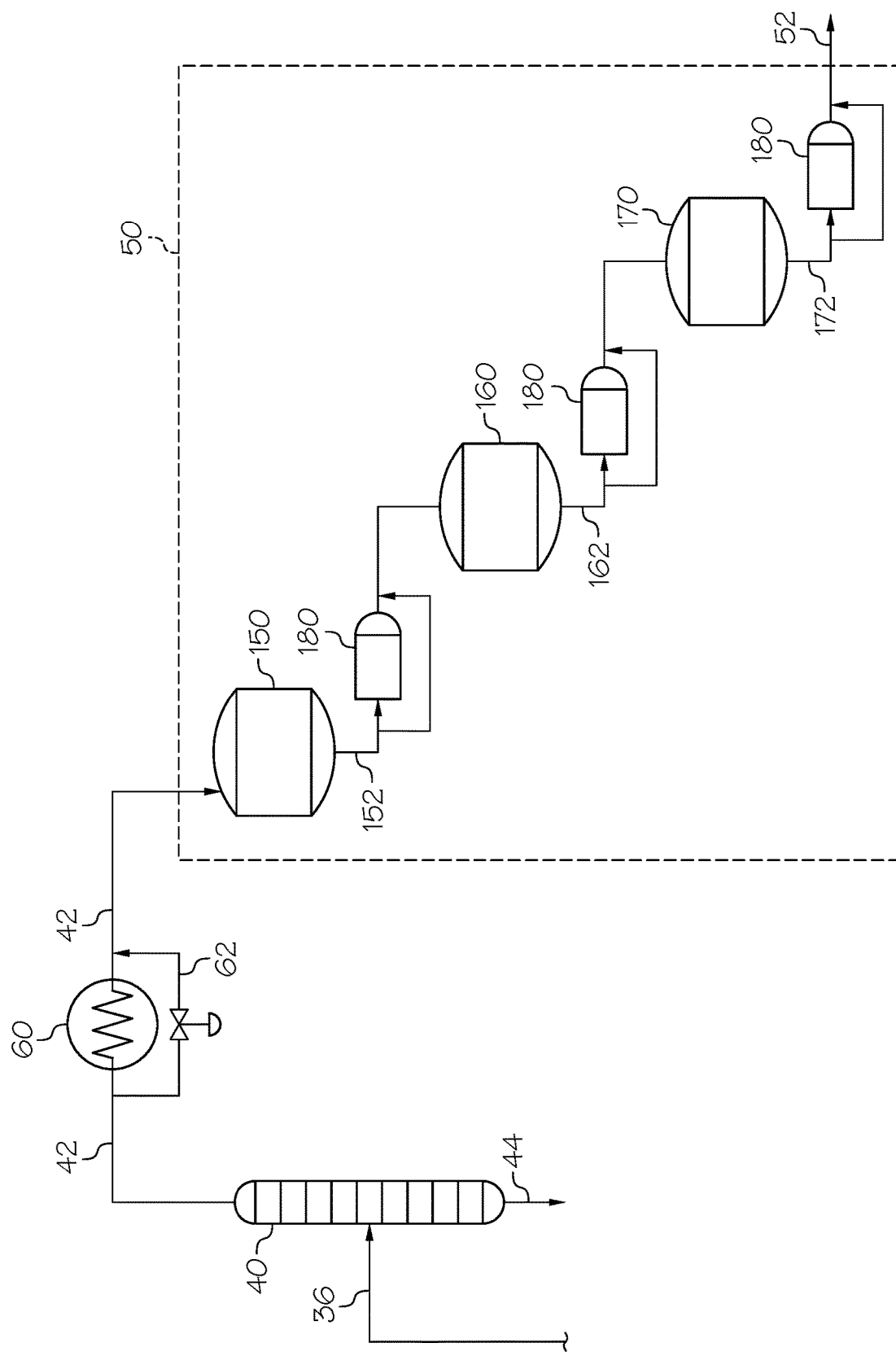
FIG. 4 schematically depicts a portion of the process of FIG. 1 in which the acetylene hydrogenation unit includes a plurality of hydrogenation reactors, according to one or more embodiments described herein.

Referring to FIG. 4, the separation system 40 and the acetylene hydrogenation unit 50 of the process 10 are depicted, the acetylene hydrogenation unit 50 including a plurality of hydrogenation reactors arranged in series (e.g., first hydrogenation reactor 150, second hydrogenation reactor 160, and third hydrogenation reactor 170). As previously discussed, the acetylene hydrogenation unit 50 can include 1, 2, 3, 4, or more than 4 hydrogenation reactors. The plurality of hydrogenation reactors of the acetylene hydrogenation unit 50 may be arranged in series, in parallel, or a combination of both. Referring to FIG. 4, the acetylene hydrogenation unit 50 is depicted as has having at least a first hydrogenation reactor 150 and a second hydrogenation reactor 160 downstream of the first hydrogenation reactor 150. The acetylene hydrogenation unit 50 may also include a third hydrogenation reactor 170 downstream of the second hydrogenation reactor 160. The acetylene hydrogenation unit 50 may also optionally include heat exchangers 180 disposed between each of the hydrogenation reactors. The heat exchangers 180 may be operable to remove heat generated from the exothermic hydrogenation reaction between the hydrogenation reactors.

Referring to FIG. 4, a method for operating an acetylene hydrogenation unit 50 having a plurality of hydrogenation reactors may include introducing the cracked gas 32 to the separation system 40, which may be operable to produce at least the hydrogenation feed 42 and the acetylene-depleted stream 44. The hydrogenation feed 42 may have any of the compositions or properties previously described herein for the hydrogenation feed 42. The method may further include contacting the hydrogenation feed 42 with an acetylene hydrogenation catalyst in the first hydrogenation reactor 150, the contacting causing hydrogenation of at least a portion of the acetylene in the hydrogenation feed 42 to produce a first hydrogenation reactor effluent 152.

The first hydrogenation reactor effluent 152 may have an acetylene concentration less than the acetylene concentration in the hydrogenation feed 42. However, the conversion of acetylene in the first hydrogenation reactor 150 may be less than or equal to 95%, less than or equal to 90%, or even less than or equal to 85%. The conversion of acetylene in the first hydrogenation reactor 150 may require one or more additional hydrogenation reactors to further convert acetylene so that the acetylene concentration in the hydrogenation effluent 52 is less than the target acetylene concentration.

Referring to FIG. 4, the method of operating the acetylene hydrogenation unit may further include contacting the first hydrogenation reactor effluent 152 with the acetylene hydrogenation catalyst in a second hydrogenation reactor 160, the contacting causing hydrogenation of a portion of the acetylene remaining in the first hydrogenation reactor effluent 152 to produce a second hydrogenation reactor effluent 162. The second hydrogenation reactor effluent 162 may have a lesser concentration of acetylene compared to the first hydrogenation reactor effluent 152. The second hydrogenation reactor effluent 162 may be passed through a heat exchanger 180 to remove heat from the exothermic hydrogenation reaction in the second hydrogenation reactor 160.

In some embodiments, the method may further include contacting the second hydrogenation reactor effluent 162 with the acetylene hydrogenation catalyst in a third hydrogenation reactor 170 to produce a third hydrogenation reactor effluent 172. The third hydrogenation reactor effluent 172 may have an acetylene concentration less than the target acetylene concentration, such as less than or equal to 2 ppmv, less than or equal to 1 ppmv, less than or equal to 0.5 ppmv, or even less than or equal to 0.1 ppmv. The third hydrogenation reactor effluent 172 may be passed out of the acetylene hydrogenation unit 50 as the hydrogenation effluent 52.

The method may further include determining a hydrogen concentration in the acetylene hydrogenation unit 50, such as by measuring the hydrogen concentration in one or more of the hydrogenation feed 42, the first hydrogenation reactor effluent 152, the second hydrogenation reactor effluent 162, or the third hydrogenation reactor effluent 172, and increasing or decreasing a temperature of the first hydrogenation reactor 150, the second hydrogenation reactor 160, the third hydrogenation reactor 170, or combinations of these. The method may include determining the temperature of the hydrogenation feed 42, the first hydrogenation reactor 150, the first hydrogenation reactor effluent 152, the second hydrogenation reactor 160, the second hydrogenation reactor effluent 162, the third hydrogenation reactor 170, or combinations of these.

The temperature of the first hydrogenation reactor 150 may be increased or decreased by increasing or decreasing, respectively, the temperature of the hydrogenation feed 42 at the inlet to the first hydrogenation reactor 150. As previously discussed, the inlet temperature of the hydrogenation feed 42 may be decreased by from 0.5° C. to 2.0° C., or from 0.5° C. to 1.5° C., or even from 0.5° C. to 1.0° C., for each incremental increase of 5 vol. % in the hydrogen concentration in the first hydrogenation reactor 150 and increased by from 0.5° C. to 2.0° C., or from 0.5° C. to 1.5° C., or even from 0.5° C. to 1.0° C., for each incremental decrease of 5 vol. % in the hydrogen concentration in the first hydrogenation reactor 150. The temperature of the second hydrogenation reactor 160 may be increased or decreased by increasing or decreasing, respectively, the temperature of the first hydrogenation reactor effluent 152 at an inlet to the second hydrogenation reactor 160. The inlet temperature of the first hydrogenation reactor effluent 152 may be decreased by from 0.5° C. to 2.0° C., or from 0.5° C. to 1.5° C., or even from 0.5° C. to 1.0° C., for each incremental increase of 5 vol. % in the hydrogen concentration in the second hydrogenation reactor 160 and increased by from 0.5° C. to 2.0° C., or from 0.5° C. to 1.5° C., or even from 0.5° C. to 1.0° C., for each incremental decrease of 5 vol. % in the hydrogen concentration in the second hydrogenation reactor 160. The temperature of the third hydrogenation reactor 170 may be increased or decreased by increasing or decreasing, respectively, the temperature of the second hydrogenation reactor effluent 162 at the inlet to the third hydrogenation reactor 170. The temperature of the second hydrogenation reactor effluent 162 may be decreased by from 0.5° C. to 2.0° C., or from 0.5° C. to 1.5° C., or even from 0.5° C. to 1.0° C., for each incremental increase of 5 vol. % in the hydrogen concentration in the third hydrogenation reactor 170 and increased by from 0.5° C. to 2.0° C., or from 0.5° C. to 1.5° C., or even from 0.5° C. to 1.0° C., for each incremental decrease of 5 vol. % in the hydrogen concentration in the first hydrogenation reactor 150. It is noted that due to the parts per million range of the concentration of acetylene, the hydrogen concentration in the hydrogenation feed 42, the first hydrogenation reactor 150, the second hydrogenation reactor 160, and third hydrogenation reactor 170 are all essentially the same.

Alternatively or additionally, the method may include increasing or decreasing the concentration of CO in the hydrogenation feed 42 based on the determination of the hydrogen concentration in the acetylene hydrogenation unit 50. The concentration of CO in the hydrogenation feed 42 may be increased by at least 10 ppmv, by at least 15 ppmv, or even by at least 20 ppmv, for each incremental increase of 5 vol. % in the hydrogen concentration in the first hydrogenation reactor 150 and decreased by at least 10 ppmv, by at least 15 ppmv, or at least by 20 ppmv for each incremental decrease of 5 vol. % in the hydrogen concentration in the first hydrogenation reactor 150. Increasing or decreasing the concentration of CO in the first hydrogenation feed may include modifying one or more operating parameters of the hydrocarbon cracking unit 20 upstream of the first hydrogenation reactor 150, as previously described herein. Increasing or decreasing the CO concentration in the hydrogenation feed 42 may also include combining the hydrogenation feed 42 with the CO-containing composition 70 to produce a mixed hydrogenation feed 72, passing the mixed hydrogenation feed 72 to the first hydrogenation reactor 150, and increasing or decreasing a proportion of the CO-containing composition 70 relative to the hydrogenation feed 42 in the mixed hydrogenation feed 72 based on the determination of the hydrogen concentration in the hydrogenation feed 42 or the first hydrogenation reactor 150.

Referring again to FIG. 1, a method for selectively hydrogenating acetylene in a cracked gas from a steam cracking unit for producing olefins may include separating the hydrogenation feed 42 from the cracked gas 36. The hydrogenation feed 42 may include acetylene, hydrogen, carbon monoxide, and at least one product. The hydrogenation feed 42 may also include any of the other constituents previously described for the hydrogenation feed 42. The method may further include contacting the hydrogenation feed 42 with an acetylene hydrogenation catalyst, the contacting causing hydrogenation of at least a portion of the acetylene of the hydrogenation feed 42 to produce the hydrogenation effluent 52. As previously discussed, the composition of the hydrocarbon feedstock 12 may be abruptly changed, which may increase or decrease the hydrogen produced in the stream cracking process. In response to a change in a composition of a hydrocarbon feedstock 12 to the steam cracking unit that results in a change in a hydrogen concentration in the hydrogenation feed 42, the method may further include determining the hydrogen concentration in the hydrogenation feed 42 and increasing or decreasing the temperature of the hydrogenation feed 42 based on the determined hydrogen concentration of the hydrogenation feed 42. Determining the hydrogen concentration of the hydrogenation feed 42 may include measuring a concentration of hydrogen in the cracked gas 36, the hydrogenation feed 42, the hydrogenation effluent 52, or combinations thereof. Increasing or decreasing the temperature of the hydrogenation feed 42 may include increasing or decreasing a temperature of the hydrogenation feed 42 prior to contact with the acetylene hydrogenation catalyst based on the determination of the hydrogen concentration in the hydrogenation feed 42. The temperature of the hydrogenation feed 42 may be decreased by from 0.5° C. to 2.0° C., or from 0.5° C. to 1.5° C., or even from 0.5° C. to 1.0° C., for each incremental increase of 5 vol. % in the hydrogen concentration in the hydrogenation feed 42 and increased by from 0.5° C. to 2.0° C., or from 0.5° C. to 1.5° C., or even from 0.5° C. to 1.0° C., for each incremental decrease of 5 vol. % in the hydrogen concentration in the hydrogenation feed 42.

In some embodiments, the method may further include increasing or decreasing a concentration of CO in the hydrogenation feed 42 based on the determination of the hydrogen concentration in the hydrogenation feed 42. The concentration of CO in the hydrogenation feed 42 may be increased by at least 10 ppmv for each incremental increase of 5 vol. % in the hydrogen concentration in the hydrogenation feed 42 and decreased by at least 10 ppmv for each incremental decrease of 5 vol. % in the hydrogen concentration in the hydrogenation feed 42. Increasing or decreasing a concentration of CO in the hydrogenation feed 42 may include increasing or decreasing an amount of sulfur-containing compounds, oxygenates such as methanol, or both introduced to the steam cracking unit (e.g., hydrocarbon cracking unit 20). Referring to FIG. 3, alternatively or additionally, increasing or decreasing an amount CO in the hydrogenation feed 42 may include combining a CO-containing composition with the hydrogenation feed 42 to form a mixed hydrogenation feed 72 and modifying the ratio of CO-containing composition to hydrogenation feed 42 to change the concentration of CO in the mixed hydrogenation feed 72. Increasing or decreasing the CO concentration in the hydrogenation feed 42 may be accompanied by a corresponding change in the temperature of the hydrogenation feed 42.

EXAMPLES

Embodiments of the present disclosure will be further clarified by the following examples, which should not be construed as limiting on the disclosed and/or claimed embodiments presently described.

A hydrogenation feed that included hydrogen, nitrogen, ethylene, propylene, carbon monoxide, and acetylene was contacted with a hydrogenation catalyst in a fixed bed reactor at a gas hourly space velocity of 11,000 hr$^{-1}$. For Example 1, the concentration of hydrogen in the hydrogenation feed was 18 volume percent, and for Example 2, the concentration of hydrogen in the hydrogenation feed was 28 volume percent. The concentrations of nitrogen, ethylene, propylene, carbon monoxide, and acetylene were maintained constant and are provided below in Table 2. Methane was used as the balance gas. The temperature of the hydrogenation feed was adjusted to obtain 94% conversion of acetylene in the hydrogenation effluent passed out of the fixed bed reactor. The temperature required to achieve 94% conversion of the acetylene and the corresponding ethylene selectivity are provided below in Table 2.

TABLE 2

| Hydrogenation Feed Properties | Example 1 | Example 2 |
| --- | --- | --- |
| Gas Hourly Space Velocity (hr$^{-1}$) | 11000 | 11000 |
| Hydrogen Concentration (vol. %) | 18 | 28 |
| N2 Concentration (vol. %) | 1.36 | 1.36 |
| Ethylene Concentration (vol. %) | 31 | 31 |
| Propylene Concentration (vol. %) | 5 | 5 |
| CO Concentration (ppmv) | 500 | 500 |
| Acetylene Concentration (ppmv) | 3000 | 3000 |
| Methane | balance | balance |
| Temperature Required for 94% Acetylene Conversion (° C.) | 50.43 | 46.97 |
| Ethylene Selectivity in Hydrogenation Effluent | 97.4 | 97.7 |

As shown by the results in Table 2, a lesser temperature of the hydrogenation feed was required to achieve 94% conversion of acetylene when the concentration of hydrogen was increased from 18% in Example 1 to 28% in Example 2. Decreasing the temperature of the hydrogenation feed from Example 1 to Example 2 maintained the ethylene selectivity at around 97%. Reducing the temperature of the hydrogenation feed at the inlet to the hydrogenation reactor may enable better heat management to minimize the reactor runaway risk and may increase the service lifetime of the catalyst, which may be subjected to less severe conditions.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for selectively hydrogenating acetylene in a cracked gas from a steam cracking unit for producing olefins, the method comprising:

separating a hydrogenation feed from the cracked gas, the hydrogenation feed comprising acetylene, hydrogen, carbon monoxide, and at least one product;

contacting the hydrogenation feed with an acetylene hydrogenation catalyst, the contacting causing hydrogenation of at least a portion of the acetylene of the hydrogenation feed to produce a hydrogenation effluent;

in response to a change in a composition of a feedstock to the steam cracking unit that results in a change in a hydrogen concentration in the hydrogenation feed, measuring a concentration of hydrogen in the hydrogenation feed, the cracked gas, or both; and increasing or decreasing a temperature of the hydrogenation feed based on the measured hydrogen concentration of the hydrogenation feed.

2. The method of claim 1, wherein increasing or decreasing the temperature of the hydrogenation feed comprises increasing or decreasing a temperature of the hydrogenation feed prior to contact with the acetylene hydrogenation catalyst based on the determination of the hydrogen concentration in the hydrogenation feed, wherein the temperature of the hydrogenation feed is decreased by from 0.5° C. to 2.0° C. for each incremental increase of 5 vol. % in the hydrogen concentration in the hydrogenation feed and increased by from 0.5° C. to 2.0° C. for each incremental decrease of 5 vol. % in the hydrogen concentration in the hydrogenation feed.

3. The method of claim 1, further comprising increasing or decreasing a concentration of CO in the hydrogenation feed based on the determination of the hydrogen concentration in the hydrogenation feed, wherein the concentration of CO in the hydrogenation feed is increased by at least 10 ppmv for each incremental increase of 5 vol. % in the hydrogen concentration in the hydrogenation feed and decreased by at least 10 ppmv for each incremental decrease of 5 vol. % in the hydrogen concentration in the hydrogenation feed.

4. The method of claim 3, wherein increasing or decreasing a concentration of CO in the hydrogenation feed comprises increasing or decreasing an amount of sulfur-containing compounds, oxygenates, or both introduced to the steam cracking unit.

5. The method of claim 1, wherein the hydrogenation feed comprises methyl acetylene and propadiene, and the at least one product comprises one or more of ethylene, propylene, methane, ethane, propane, or combinations of these.

6. The method of claim 1, wherein the hydrogenation effluent has a concentration of acetylene of less than or equal to 2 ppmv.

7. A method for operating an acetylene hydrogenation unit in an olefin production system, the process comprising:

cracking at least a portion of a feedstock in a steam cracking unit to produce a cracked gas, the feedstock comprising one or more hydrocarbons;

passing at least a portion of the cracked gas to a separation system operable to produce at least a hydrogenation feed from the cracked gas, the hydrogenation feed comprising acetylene, carbon monoxide, hydrogen, and at least one product;

contacting the hydrogenation feed with an acetylene hydrogenation catalyst in an acetylene hydrogenation unit, the contacting causing hydrogenation of at least a portion of the acetylene in the hydrogenation feed to produce a hydrogenation effluent;

changing a composition of the feedstock cracked in the steam cracking unit, wherein changing the composition of the feedstock increases or decreases a hydrogen concentration in the hydrogenation feed;

in response to changing the composition of the feedstock, determining the hydrogen concentration in the acetylene hydrogenation unit; and increasing or decreasing a temperature of the acetylene hydrogenation unit based on the determination of the hydrogen concentration in the acetylene hydrogenation unit.

8. The method of claim 7, wherein determining the hydrogen concentration in the acetylene hydrogenation unit comprises measuring a concentration of hydrogen in the cracked gas, the hydrogenation feed, or combinations thereof.

9. The method of claim 8, wherein the acetylene hydrogenation unit comprises at least a first hydrogenation reactor and a second hydrogenation reactor downstream of the first hydrogenation reactor, and wherein a conversion of acetylene in the first hydrogenation reactor is less than or equal to 95%.

10. The method of claim 9, wherein the acetylene hydrogenation unit comprises at third hydrogenation reactor downstream of the second hydrogenation reactor.

11. The method of claim 7, wherein increasing or decreasing the temperature of the acetylene hydrogenation unit comprises increasing or decreasing a temperature of the hydrogenation feed passed to the acetylene hydrogenation unit based on the determination of the hydrogen concentration in the acetylene hydrogenation unit, wherein the temperature of the hydrogenation feed is decreased by from 0.5° C. to 2.0° C. for each incremental increase of 5 vol. % in the hydrogen concentration in the acetylene hydrogenation unit and increased by from 0.5° C. to 2.0° C. for each incremental decrease of 5 vol. % in the hydrogen concentration in the acetylene hydrogenation unit.

12. The method of claim 7, further comprising increasing or decreasing the concentration of CO in the acetylene hydrogenation unit based on the determination of the hydrogen concentration in the acetylene hydrogenation unit, wherein the concentration of CO in the acetylene hydrogenation unit is increased by at least 10 ppmv for each incremental increase of 5 vol. % in the hydrogen concentration in the acetylene hydrogenation unit and decreased by at least 10 ppmv for each incremental decrease of 5 vol. % in the hydrogen concentration in the acetylene hydrogenation unit.

13. The method of claim 12, wherein increasing or decreasing the concentration of CO in the acetylene hydrogenation unit comprises increasing or decreasing a concentration of CO in the hydrogenation feed.

14. The method of claim 13, wherein increasing or decreasing the concentration of CO in the hydrogenation feed comprises increasing or decreasing an amount of sulfur-containing constituents, oxygenates, or both introduced to the steam cracking unit.

15. The method of claim 7, wherein the hydrogenation feed comprises methyl acetylene and propadiene, and the at least one product comprises one or more of ethylene, propylene, methane, ethane, propane, or combinations of these.

16. The method of claim 7, wherein the hydrogenation effluent has a concentration of acetylene of less than or equal to 2 ppmv.

17. A method for selectively hydrogenating acetylene in a cracked gas from a steam cracking unit for producing olefins, the method comprising:

separating a hydrogenation feed from the cracked gas, the hydrogenation feed comprising acetylene, hydrogen, carbon monoxide, and at least one product;

contacting the hydrogenation feed with an acetylene hydrogenation catalyst, the contacting causing hydrogenation of at least a portion of the acetylene of the hydrogenation feed to produce a hydrogenation effluent;

in response to a change in a composition of a feedstock to the steam cracking unit that results in a change in a hydrogen concentration in the hydrogenation feed, determining the hydrogen concentration in the hydrogenation feed;

increasing or decreasing a temperature of the hydrogenation feed based on the determined hydrogen concentration of the hydrogenation feed; and increasing or decreasing a concentration of CO in the hydrogenation feed based on the determination of the hydrogen concentration in the hydrogenation feed, wherein the concentration of CO in the hydrogenation feed is increased by at least 10 ppmv for each incremental increase of 5 vol. % in the hydrogen concentration in the hydrogenation feed and decreased by at least 10 ppmv for each incremental decrease of 5 vol. % in the hydrogen concentration in the hydrogenation feed.

* * * * *